United States Patent [19]

Flashner

[11] Patent Number: 4,469,630
[45] Date of Patent: Sep. 4, 1984

[54] PURIFICATION OF MONOCLONAL ANTIBODIES

[75] Inventor: Michael Flashner, Easton, Pa.

[73] Assignee: J. T. Baker Chemical Co., Phillipsburg, N.J.

[21] Appl. No.: 555,023

[22] Filed: Nov. 25, 1983

[51] Int. Cl.³ .................... C07G 7/00; A61K 39/395
[52] U.S. Cl. .................. 260/112 B; 260/112 R; 424/85; 435/69; 435/70; 435/172.2; 435/240; 435/241; 435/68; 436/548; 935/15; 935/103
[58] Field of Search .............. 260/112 R, 112 B; 424/85; 435/68, 69, 70, 172.2, 240, 241; 436/548

[56] References Cited

U.S. PATENT DOCUMENTS

| | | | |
|---|---|---|---|
| 4,196,265 | 4/1980 | Koprowski et al. | 435/240 X |
| 4,271,145 | 6/1981 | Wands et al. | 435/172.2 X |
| 4,350,683 | 9/1982 | Galfré et al. | 424/85 |
| 4,361,509 | 11/1982 | Zimmerman et al. | 260/112 B |
| 4,361,550 | 11/1982 | Kung et al. | 424/85 |
| 4,381,295 | 4/1983 | Kung et al. | 260/112 R X |
| 4,423,147 | 12/1983 | Secher et al. | 435/68 |
| 4,427,653 | 1/1984 | Springer | 424/85 |

OTHER PUBLICATIONS

J. Chromatography 185, 375–392, (1978), Alpert et al.
Anal. Biochem. 121, 156–159, (1982), Vanecek et al.
Methods in Enzymology, Galfred et al., vol. 73, pp. 31–46, 1981, Academic Press.

Primary Examiner—Howard E. Schain
Attorney, Agent, or Firm—Salvatore R. Conte

[57] ABSTRACT

A method of chromatographically separating monoclonal antibody type IgG from mouse ascites fluid utilizing a particular chromatographic packing of silica gel bearing bound polyethylenimine functions.

5 Claims, No Drawings

PURIFICATION OF MONOCLONAL ANTIBODIES

The invention relates to a method of purifying the monoclonal antibody content of a mouse ascites fluid sample. More particularly, the present invention is concerned with a method of separating and purifying monoclonal antibody type IgG from mouse ascites fluid utilizing liquid column chromatography on a particular stationary porous phase of silica gel bearing bound polyethylenimine (PEI) functions and gradient elution of the monoclonal antibody from the polyethylenimine bound column with aqueous buffer of from about pH 6.0 to about pH 8.3.

The particular stationary porous phase of silica gel bearing bound polyethylenimine functions, that is, the chromatographic packing utilized in this invention, are of two types.

The preferred type is described in U.S. patent application Ser. No. 555,368, filed by Hugh Ramsden on even date herewith and entitled "Polyethylenimine Bound Chromatographic Packing", the content of which is incorporated herein by reference. Relevant text of this application is reproduced below.

The second type is the adsorbed cross-linked PEI-silica gel stationary phase described by G. Vanecek & F. E. Regnier, Anal. Biochem. 121, 156–159 (1982) and A. J. Alpert & F. E. Regnier, J. Chromatogr. 185, 375–392 (1978), which type is commercially available from SynChrom, Inc. of Linden, Ind., under the brand name "SynChropak". Alpert and Regnier have shown that polyethyleneimine (PEI) may be adsorbed to silica gel surfaces and crosslinked to form a stable polyamine layer. The structure of PEI provides sufficient primary and secondary amino groups that adjacent adsorbed PEI molecules on the surface of silica gel may be crosslinked by multifunctional oxiranes into a polymeric layer. Through the use of a hydrophilic crosslinker such as diglycidylethylene glycol, a hydrophilic coating may be produced.

DETAILED DESCRIPTION OF (RAMSDEN) INVENTION

The non-crosslinked covalently bound PEI silica gel products of the present invention are conveniently prepared in accordance with the following steps:

A. reacting particulate silica gel having an average particle diameter of from about 3 to about 70 microns and an average pore size of from about 50 to about 1000 Angstrom units in an inert organic solvent slurry with a lower alkanolic solution of polyethyleniminopropyl trimethoxy silane having an average molecular weight of from about 400 to about 1800, said reaction being conducted at ambient to refluxing temperature for about 2 to about 50 hours;

B. recovering the resultant solid fraction from the reaction mixture; and

C. heating said solid fraction at a temperature and for a time sufficient to dry and completely bond the silane to the silica gel.

As used herein, the term "covalently bound" or "covalently bonded" means that the PEI moieties are covalently attached to the silica gel by way of chemical interaction resulting in a propyl-silyl (Pr-Si) linkage; and the term "non-crosslinked" means that the imino and amino groups on adjacent covalently bound PEI moieties are not crosslinked, or reacted with a crosslinking agent, to form a polymeric layer.

Without being bound thereby, it is believed that the reaction proceeds to completion in two steps as follows:

Step 1: Silica hydroxyls and the methoxy groups on the silane react to form Si-O-Si bonds and free methanol, with some residual methoxy groups remaining unreacted:

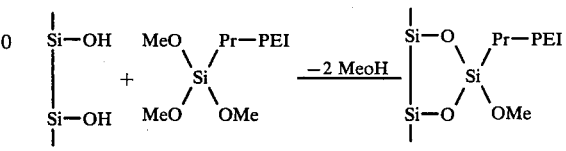

Step 2: Completion of the reaction with the residual methoxy groups is effected during heat curing by (a) and (b):

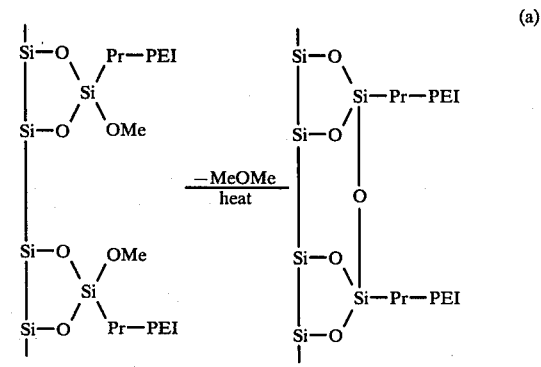

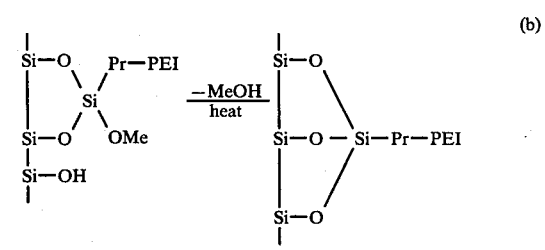

Silica gel, consisting of amorphous silica, is commercially available in irregular and spherical (preferred) particulate forms and in several commercial grades with mesh sizes ranging from 3 through 325 (ASTM). Rather than relying upon a numerical indication of mesh size, however, more accurate indicia for purposes of this invention are the average diameter and average pore size of the silica gel particles, respectively, from about 3 to about 70 microns and from about 50 to about 1000, preferably 250–500, Angstrom units. For end product use in packing HPLC chromatographic columns, a silica gel starting material of from about 3 to about 10 microns is preferred, and, for packing low pressure chromatographic columns, from about 40 to about 70 microns is preferred.

Among the inert organic solvents suitable for preparing the silica gel slurry are aliphatic hydrocarbons such as, for example, hexane, heptane and the like; aromatic hydrocarbons such as, for example, benzene, toluene, xylene and the like; lower alkanols such as, for example, ethanol, isopropanol, butanol and the like; chlorinated methanes such as, for example, methylene chloride, chloroform, carbon tetrachloride and the like (Caution: such chloro solvents may react at higher temperatures!); and such other inert solvents as tetrahydrofuran, glyme, diglyme and the like. In general a 1:5 ratio of silica gel in grams to solvent in milliliters affords a suitable slurry. Due to the fine, insoluble nature of the particulate silica gel a slurry rather than a true solution is obtained.

Polyethyleniminopropyl trimethoxy silane, also known as (N-trimethoxysilylpropyl)-polyethylenimine, is the reaction product of polyethylenimine and aminopropyltrimethoxy silane and can be represented by the following formula:

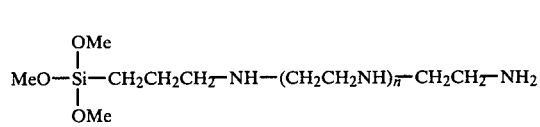
(I)

wherein, for purposes of this invention, n is an integer from about 4 to about 37, or, if expressed in terms of average molecular weight, from about 400 to about 1800.

The silane (I) is used in the reaction with the silica gel in the form of a lower $C_1-C_6$ alkanolic solution using sufficient alkanol to solubilize the silane. A fifty percent w/w isopropanolic solution is preferred. In general, about 25-100 grams of the silane, or, alternatively, about 50-200 ml of a fifty percent w/w alkanolic solution of the silane, is used to react with each 100 grams silica gel. The reaction may be conducted at ambient temperature although elevated temperatures up to the refluxing temperature of the reaction solvent system may be utilized to enhance the rate of reaction. The reaction proceeds readily to substantial completion (Step 1) within 2-50 hours. Stirring during admixture of the reactants is advantageously employed although the reaction thereafter may continue without further stirring. Anhydrous conditions are not critical, it having been found that the presence of a small amount of water, for example, about 0.1-1.0 ml per 50 ml of the slurry solvent, does not adversely affect the reaction.

The resultant solid fraction is recovered from the reaction mixture by conventional physical means, for example, filtration, centrifugation, etc. In general, a filtering means sufficient to retain a particle size of 5 microns is suitable whereas centrifuging is suitable for a particle size of 3 microns.

The recovered solid fraction is then heat cured at a temperature and for a time sufficient to dry and completely bond the silane to the silica gel covalently. In general, from about 1-4 hours at about 40°-120° C. has been found sufficient. The thus-obtained covalently bound, non-crosslinked final product preferably contains from about 0.5 to about 3.8 percent nitrogen.

For purposes of this invention, the chromatographic packing, hereinafter sometimes referred to as "PEI-silica gel" for purposes of convenience, is utilized wherein the starting silica gel is limited to one having an average particle diameter of from about 3 to about 40 microns. The average pore size may be from about 50 to about 1000 Angstrom units, although an average pore size greater than 250 Angstroms is preferred.

Accordingly, the instant invention provides a method of obtaining essentially homogeneous monoclonal antibody type IgG from a sample of mouse ascites fluid containing said monoclonal antibody by employing liquid chromatographic means wherein the chromatographic packing comprises particulate silica gel having an average particle diameter of from about 3 to about 40 microns and an average pore size of from about 50 to about 1000 Angstrom units to which polyethylenimine functions are bound, either in adsorbed crosslinked form according to Regnier et al., ibid, or in covalently bound non-crosslinked form according to Ramsden, ibid. Regarding the latter, the PEI-silica gel chromatographic packing is the reaction product of the aforementioned particulate silica gel with polyethyleniminopropyl trimethoxy silane having an average molecular weight of from about 400 to about 1800.

It has now been found that such chromatographic packing is particularly suitable for use in liquid chromatography, particularly high performance liquid chromatography (HPLC), for binding type IgG monoclonal antibodies and other proteins in mouse ascites fluid containing same, thereby allowing preferential separation of the bound proteins by gradient elution using appropriate aqueous buffers. There are thus obtained a number of protein components which are originally present in the ascites fluid including the essentially homogeneous monoclonal antibody of interest. As used herein "essentially homogeneous" means that >90% of the protein present in the quantitatively recovered IgG antibody eluant fraction is the particular IgG monoclonal antibody. The percent purity may be verified by known procedures in the art, such as, for example, by sodium dodecyl sulfate polyacrylamide gel electrophoresis, see U. K. Laemmli, Nature, 227, 680 (1970).

The instant invention is suitable for use with mouse ascites fluid containing monoclonal antibody of all subclasses of the IgG type, for example, $IgG_1$, $IgG_{2a}$ and $IgG_{1+3}$ and the like. The methodology of preparing such mouse ascites fluid containing monoclonal antibody is common to the art, for example, see "Monoclonal Antibodies, Hybridomas; A New Dimension in Biological Analyses", by R. H. Kennet et al., published by Plenum Press, N.Y. 1980; and "Methods in Enzymology" by G. Galfred and C. Milstein, edited by J. J. Langone and H. Van Vunakis, Vol. 73, p. 31–46, publ. by Academic Press, 1981.

The isolation of monoclonal antibody in highly purified form is obviously desirable. For example, for in vivo therapeutic purposes, monoclonal antibody as pure and as concentrated as possible is required to minimize adverse side effects and to maximize the intended therapeutic purpose. Similarly, for in vitro diagnostic purposes, such purified and concentrated monoclonal antibody is desirable to maximize the sensitivity and specificity of the particular diagnostic test.

Before the mouse ascites fluid can be used for this invention, it is pre-treated to remove interfering particulate matter and is equilibrated to the appropriate ionic strength and pH necessary to achieve binding of the monoclonal antibody to the PEI-silica gel support. The particulate matter can be removed by conventional clarifying means, for example, by filtration or by centrifugation at a force sufficient to pelletize the particulate material. Equilibration of the particulate-free mouse ascites fluid can be achieved by any means common to the state-of-the-art, for example, by chromatographic desalting with an appropriate buffer on molecular sieves of appropriate type and pore size such as those commercially available under the brand name "Sephadex", by dialysis against an appropriate buffer, and the like, to equilibrate the mouse ascites fluid to a pH greater than the pI (that pH at which the monoclonal antibody carries no net ionic charge in its environment) of the particular IgG monoclonal antibody and to an ionic strength equal to or less than the ionic strength of the lower ionic strength buffer used for gradient elution in the subsequent chromatographic treatment of the mouse ascites fluid.

Chromatographic columns suitable for use in liquid chromatography, preferably HPLC, are packed with the previously described porous PEI-silica gel solid support. Suitable steel or glass chromatographic columns include those having dimensions of about 5–100 cm in length and internal diameters of about 1–100 mm. Selection of the proper chromatographic parameters such as, for example, column packing technique, column size, column temperature, pressure and the like, are readily determined by one of ordinary skill in the art.

The packed column is equilibrated in a chromatograph by passing an appropriate buffer solution through the column. After this buffer-equilibration step, the column is used to make the chromatographic separation of the proteinaceous components of the mouse ascites fluid which, as noted, previously has been freed of particulate matter and has been equilibrated to the appropriate ionic strength and pH. A sample of such pretreated mouse ascites fluid is then applied to the buffer-equilibrated column to bind its component proteins to the PEI-silica gel packing.

The bound proteins can then be selectively eluted by conventional gradient elution techniques, taking into consideration the interdependent chromatographic parameters of time, flow-rate and gradient shape to generate gradients of increasing ionic strength or decreasing pH. Anionic buffers, for example, potassium phosphate, tris-acetate, ammonium acetate and the like, of from about pH 6.0 to about 8.3, can be used to generate such gradients to elute the bound proteins from the polyethyleneimine function. For example, the gradient can be advantageously formed from about one-half hour to about four hours with a flow rate of from about 0.1 mL/min to about 2 L/min.

The resolved proteins can be identified by any means common to the state-of-the-art, for example, by monitoring the ultraviolet absorbance at 280 nm. The eluent fractions containing the separated proteins can be collected by use of a fraction collector. The eluent fraction containing the homogeneous monoclonal antibody can be identified by means well-established in the art such as, for example, by a radioimmunoassay developed for the particular antibody, by other antibody-antigen reactions, or by polyacrylamide gel electrophoresis.

The process of this invention has been found to be independent of the total volume of the mouse ascites fluid containing the monoclonal antibody and there is no limiting factor except for the amount of PEI-silica gel used as the chromatographic packing, that is, the process is operable so long as the capacity of the solid chromatographic support is not surpassed.

In accordance with the method of the present invention, therefore, a sample of mouse ascites fluid containing monoclonal antibody type IgG is chromatographically separated to provide said antibody in essentially homogeneous form. As more fully described heretofore, the preferred method comprises purifying a sample of particulate-free mouse ascites fluid containing such monoclonal antibody by:

a. equilibrating said sample of particulate-free mouse ascites fluid to an ionic strength equal to or less than the ionic strength of the lower ionic strength buffer, used for gradient elution in the subsequent chromatographic separation and recovery step and to a pH greater than the pI of the particular IgG monoclonal antibody; and b. separating and recovering said monoclonal antibody type IgG from said sample by employing liquid chromatographic means wherein the chromatographic packing consists essentially of the reaction product of particulate silica gel having an average particle diameter of from about 3 to about 40 microns and an average pore size of from about 50 to about 1000 Angstrom units with polyethyleniminopropyl trimethoxy silane having an average molecular weight of from about 400 to about 1800.

The invention will be more easily understood with the aid of the examples which follow below which are given solely as an illustration of the present invention and are not limitative of the same.

EXAMPLE 1

A slurry of 20 grams silica gel with average particle diameter of 5.25 microns and average pore size of 330 Angstroms, commercially available from The Sep A Ra Tions Group, Hesperia, CA, as a spherical silica under the trademark "Vydac A", Catalog No. 101T9B5, in 100 ml toluene and 2 ml water is prepared and stirred for 10 minutes at room temperature. To this is added with stirring 39.4 grams of a 50% w/w isopropanolic solution of polyethyleniminopropyl trimethoxy silane having an average molecular weight of 500 and the mixture is stirred for an additional 5 minutes. The mixture is then allowed to stand overnight at room temperature. The mixture is next filtered using a 1.0 micron filter funnel. The filtrate is washed with 50 ml toluene twice and 50 ml methanol twice, then air dried on the funnel and finally oven dried at 80°–85° C. for about 3 hr. 30 min. to yield the covalently bound, non-crosslinked PEI-silica gel product; about 2.85% N.

EXAMPLE 2

A 2 mL sample of mouse ascites fluid containing a monoclonal antibody specific for bacterial lipopolysaccharide cell wall and belonging to the subclass IgG$_1$, as determined by conventional subclass specific antisera, was centrifuged at 15,600×gravity for 5 minutes. The supernatant fluid was then equilibrated to 10 mM potassium phosphate buffer, pH 6.73, by dialysis overnight (about 17 hours) against 2 1-liter changes of the 10 mM potassium phosphate buffer, pH 6.73. A stainless steel chromatographic column, 25 cm×0.46 mm, was packed with 3.8 g of the PEI-silica gel product obtained from Example 1 and equilibrated with 0.01M potassium phosphate buffer, pH 6.73, by pumping this buffer through the column at a flow rate of 1 mL/min for 20 minutes. A 0.25 mL equilibrated sample of mouse ascites fluid was applied to the polyethyleneimine-bound silica gel column and protein separation was achieved by gradient elution using a 60 minute linear gradient from 0.01M potassium phosphate, pH 6.73, to 0.25M potassium phosphate, pH 6.8, at a flow rate of 1 mL/min. Protein elution was detected using UV absorbance at 280 nm with full scale absorbance set at 0.64 absorbance units. A series of 280 nm absorbing peaks were detected ranging in retention time from about 3 minutes to about 25 minutes. The protein peak at about 16 minutes was identified as the antilipopolysaccharide monoclonal antibody by co-chromatographing with a homogeneous sample of the same monoclonal antibody using the identical gradient profile as outlined above.

The protein peak eluting at about 16 minutes was evaluated to be greater than 90% pure by two criteria. First, the collected protein peak gave a symmetrical peak after chromatogaphy on the polyethyleneimine-bound silica gel column, according to F. B. Regnier, Science 222, 245 (1983). Second, sodium dodecyl sulfate polyacrylamide gel electrophoresis, performed essentially as described by U. K. Laemmli, Nature, 227, 680 (1970), gave two major coomassie blue bands corresponding to molecular weights of 50,000 daltons (heavy chain of IgG) and 25,000 daltons (light chain of IgG) and a third faint coomassie blue band representing less than 10% of the total stained protein.

EXAMPLE 3

A 2 mL sample of mouse ascites fluid containing a monoclonal antibody specific for myosin and belonging to the subclass $IgG_{2a}$ as determined by conventional subclass specific antisera, was centrifuged at $15,600 \times$ gravity for 5 minutes. The supernatant fluid was then equilibrated to 10 mM potassium phosphate buffer, pH 6.73, by dialysis overnight against 2 1-liter changes of the 10 mM potassium phosphate buffer, pH 6.73. A stainless steel chromatogaphic column, 25 cm $\times$ 0.46 mm, was packed with 3.8 g of the PEI-silica gel product obtained from Example 1 and equilibrated with 0.01M potassium phosphate buffer, pH 6.73, by pumping this buffer through the column at a flow rate of 1 mL/min for 20 minutes. A 0.25 mL equilibrated sample of mouse ascites fluid was applied to the polyethyleneimine-bound silica gel column and protein separation was achieved by gradient elution using a 60 minute linear gradient from 0.01M potassium phosphate, pH 6.73, to 0.25M potassium phosphate, pH 6.8, at a flow rate of 1 mL/min. Protein elution was detected using UV absorbance at 280 nm with full scale absorbance set at 0.64 absorbance units. A series of 280 nm absorbing peaks were detected ranging in retention times from about 3 minutes to about 25 minutes. The protein peak at about 16 minutes was identified as the antimyosin monoclonal antibody by co-chromatographing with a homogeneous sample of the same monoclonal antibody using the identical gradient profile as outlined above. The protein peak eluting at about 16 minutes was evaluated to be greater than 90% pure by the two criteria set forth in Example 2.

EXAMPLE 4

A 2 mL sample of mouse ascites fluid containing an IgG monoclonal antibody of unknown specificity was centrifuged at $15,600 \times$ gravity for 5 minutes. The supernatant fluid was then equilibrated to 10 mM potassium phosphate, pH 6.73, buffer, by dialysis overnight against 2 1-liter changes of the 10 mM potassium phosphate buffer, pH 6.73. A stainless steel chromatographic column 25 cm $\times$ 0.46 mm was packed with 3.8 g of the polyethyleneimine silica gel product of Example 1 and equilibrated with 0.01M potassium phosphate buffer, pH 6.73, by pumping this buffer through the column at a flow rate of 1 mL/min for 20 minutes. A 0.25 mL equilibrated sample of mouse ascites fluid was applied to the polyethyleneimine-silica gel column and separation was achieved by gradient elution by using a 60 minute linear gradient from 0.01 potassium phosphate, pH 6.73, to 0.25M potassium phosphate, pH 6.8. Protein elution was detected using UV absorbances at 280 nm with full scale absorbance set at 0.64 absorbance units. A series of 280 nm absorbing peaks were detected ranging in retention times from about 3 minutes to about 25 minutes. The protein peak at about 16 minutes was identified as the monoclonal antibody by co-chromatographing with a homogeneous sample of the same monoclonal antibody using the identical gradient profile as outlined above.

The protein peak eluting at about 16 minutes was evaluated to be greater than 95% pure by polyacrylamide gel electrophoresis performed as described by O. Gabriel, "Methods in Enzymology", edited by W. B. Jakaby, Vol. 22, p. 565–578, publ. by Academic Press, 1971, which gave a single coomassie blue band. The mobility of this band corresponds to that observed for standard monoclonal antibodies.

EXAMPLE 5

A stainless steel chromatographic column, 25 cm $\times$ 4.6 mm, was packed with 3.8 g of polyethyleneimine bound silica gel of Example 1 and equilibrated with 0.01M potassium phosphate, pH 6.73, by pumping this buffer through the column at a flow rate of 1 mL/min for 20 minutes. A 6 uL equilibrated sample of the same mouse ascites fluid utilized in Example 2 was applied to the PEI-silica gel column and separation was achieved by gradient elution using a 120 minute linear gradient from 0.01M potassium phosphate, pH 6.73, to 0.25M potassium phosphate, pH 6.8, at a flow rate of 1 mL/min. Protein elution was detected using UV absorbances at 280 nm with full scale absorbance set at 0.01 absorbance units. A series of 280 nm absorbing peaks were detected ranging in retention times from about 3 minutes to about 50 minutes. The protein peak at about 28 minutes was identified as the antilipopolysaccharide monoclonal antibody by co-chromatographing with a homogeneous sample of the same monoclonal antibody using the identical gradient profile as outlined above.

EXAMPLE 6

A stainless steel chromatographic column, 25 cm $\times$ 4.6 mm, was packed with 3.8 g of polyethyleneimine bound silica gel of Example 1 and equilibrated with 0.01M potassium phosphate, pH 8.3, by pumping this buffer through the column at a flow rate of 1 mL/min. for 30 minutes. A 6 uL equilibrated sample of the same mouse ascites fluid utilized in Example 2 was applied to the PEI-silica gel column and separation was achieved by gradient elution using a 60 minute linear gradient from 0.01M potassium phosphate, pH 8.3, to 0.25M potassium phosphate, pH 8.3, at a flow rate of 1 mL/min. Protein elution was detected using UV absorbance at 280 nm with full scale absorbance set at 0.01 absorbance units. A series of 280 nm absorbing peaks were detected ranging in retention times from about 3 minutes to about 50 minutes. The protein peak at about 12 minutes was identified as the antilipopolysaccharide monoclonal antibody by co-chromatographing with a homogeneous sample of the same monoclonal antibody using the identical gradient profile as outlined above.

EXAMPLE 7

A stainless steel chromatographic column, 25 cm $\times$ 4.6 mm, was packed with 3.8 g of polyethyleneimine bound silica gel of Example 1 and equilibrated with 0.01M potassium phosphate, pH 6.0, by pumping this buffer through the column at a flow rate of 1 mL/min.

for 20 minutes. A 6 uL equilibrated sample of the same mouse ascites fluid utilized in Example 2 was applied to the PEI-silica gel column and separation was achieved by gradient elution using a 60 minute linear gradient from 0.01M potassium phosphate, pH 6.0, to 0.25M potassium phosphate, pH 6.0, at a flow rate of 1 mL/min. Protein elution was detected using UV absorbance at 280 nm with full scale absorbance set at 0.01 absorbance units. A series of 280 nm absorbing peaks were detected ranging in retention times from about 3 minutes to about 14 minutes. The protein peak at about 12 minutes was identified as the antilipopolysaccharide monoclonal antibody by co-chromatographing with a homogeneous sample of the same monoclonal antibody using the identical gradient profile as outlined above.

EXAMPLE 8

A stainless steel chromatographic column, 25 cm×4.6 mm, was packed with 3.8 g of polyethyleneimine bound silica gel of Example 1 and equilibrated with 0.01M ammonium acetate, pH 6.79, by pumping this buffer through the column at a flow rate of 1 mL/min. for 30 minutes. A 6 uL equilibrated sample of the same mouse ascites fluid utilized in Example 2 was applied to the PEI-silica gel column and separation was achieved by gradient elution using a 30 minute linear gradient from 0.01M ammonium acetate, pH 6.79, to 1.0M ammonium acetate, pH 6.79, at a flow rate of 1 mL/min. Protein elution was detected using UV absorbance at 280 nm with full scale absorbance set at 0.01 absorbance units. A series of 280 nm absorbing peaks were detected ranging in retention times from about 3 minutes to about 25 minutes. The protein peak at about 12 minutes was identified as the antilipopolysaccharide monoclonal antibody by co-chromatographing with a homogeneous sample of the same monoclonal antibody using the identical gradient profile as outlined above.

EXAMPLE 9

A SynChrom, Inc., SnyChropak AX300 chromatographic column (25 cm×4.1 mm) was equilibrated with 0.01M potassium phosphate, pH 6.73, by pumping this buffer through the column at a flow rate of 1 mL/min for 20 minutes. A 6 uL equilibrated sample of the same mouse ascites fluid of Example 2 was applied to the column and separation was achieved by gradient elution using a 60 minute linear gradient from 0.01M potassium phosphate, pH 6.73, to 0.25M potassium phosphate, pH 6.8, at a flow rate of 1 mL/min. Protein elution was detected using UV absorbance at 280 nm with full scale absorbance set at 0.01 absorbance units. A series of 280 nm absorbing peaks were detected ranging in retention times from about 3 minutes to about 30 minutes. The protein peak at about 20 minutes was identified as the antilipopolysaccharide monoclonal antibody by co-chromatographing with a homogeneous sample of the same monoclonal antibody using the identical gradient profile as outlined above.

I claim:

1. A method of obtaining essentially homogeneous monoclonal antibody type IgG from a sample of mouse ascites fluid containing said monoclonal antibody which comprises separating and recovering said monoclonal antibody from said sample by employing liquid chromatographic means wherein the chromatographic packing consists essentially of particulate silica gel having an average particle diameter of from about 3 to about 40 microns and an average pore size of from about 50 to about 1000 Angstrom units to which polyethylenimine functions are bound in covalently bound non-crosslinked form or in adsorbed crosslinked form.

2. A method of obtaining essentially homongeneous monoclonal antibody type IgG from a sample of mouse ascites fluid containing said monoclonal antibody which comprises separating and recovering said monoclonal antibody from said sample by employing liquid chromatographic means wherein the chromatographic packing consists essentially of the reaction product of particulate silica gel having an average particle diameter of from about 3 to about 40 microns and an average pore size of from about 50 to about 1000 Angstrom units with polyethyleniminopropyl trimethoxy silane having an average molecular weight of from about 400 to about 1800.

3. A method of obtaining essentially purified monoclonal antibody type IgG from a sample of particulate-free mouse ascites fluid containing said monoclonal antibody which comprises:

a. equilibrating said sample of particulate-free mouse ascites fluid to an ionic strength equal to or less than the ionic strength of the lower ionic strength buffer used for gradient elution in the subsequent chromatographic separation and recovery step and to a pH greater than the pI of the particular monoclonal antibody; and b. separating and recovering said monoclonal antibody type IgG from said sample by employing liquid chromatographic means wherein the chromatographic packing consists essentially of the reaction product of particulate silica gel having an average particle diameter of from about 3 to about 40 microns and an average pore size of from about 50 to about 1000 Angstrom units with polyethyleniminopropyl trimethoxy silane having an average molecular weight of from about 400 to about 1800.

4. A method of obtaining essentially homongeneous monoclonal antibody type IgG from a sample of mouse ascites fluid containing said monoclonal antibody which comprises separating and recovering said monoclonal antibody from said sample by employing liquid chromatographic means wherein the chromatographic packing consists essentially of particulate silica gel having an average particle diameter of from about 3 to about 40 microns and an average pore size of from about 50 to about 1000 Angstrom units to which polyethylenimine functions are bound in adsorbed crosslinked form.

5. A method of obtaining essentially purified monoclonal antibody type IgG from a sample of particulate-free mouse ascites fluid containing said monoclonal antibody which comprises:

a. equilibrating said sample of particulate-free mouse ascites fluid to an ionic strength equal to or less than the ionic strength of the lower ionic strength buffer used for gradient elution in the subsequent chromatographic separation and recovery step and to a pH greater than the pI of the particular monoclonal antibody; and b. separating and recovering said monoclonal antibody type IgG from said sample by employing liquid chromatographic means wherein the chromatographic packing consists essentially of particulate silica gel having an average particle diameter of from about 3 to about 40 microns and an average pore size of from about 50 to about 1000 Angstrom units to which polyethylenimine functions are bound in adsorbed crosslinked form.

* * * * *